(12) United States Patent
Walker et al.

(10) Patent No.: US 7,405,044 B2
(45) Date of Patent: Jul. 29, 2008

(54) MULTIPLEX PCR FOR SIMULTANEOUS QUANTITATION OF HUMAN NUCLEAR, MITOCHONDRIAL, AND MALE Y-CHROMOSOME DNA

(75) Inventors: Jerilyn A. Walker, Breaux Bridge, LA (US); Dale J. Hedges, Plaquemine, LA (US); Jaiprakash G. Shewale, New Orleans, LA (US); Sudhir K. Sinha, New Orleans, LA (US); Mark A. Batzer, Mandeville, LA (US)

(73) Assignees: Reliagene Technologies Inc., New Orleans, LA (US); Board of Supervisors of Louisiana State University and Agricultural and Mechanical College, Baton Rouge, LA (US)

( * ) Notice: Subject to any disclaimer, the term of this patent is extended or adjusted under 35 U.S.C. 154(b) by 0 days.

(21) Appl. No.: 11/245,444

(22) Filed: Oct. 7, 2005

(65) Prior Publication Data
US 2006/0099620 A1 May 11, 2006

Related U.S. Application Data

(60) Provisional application No. 60/616,852, filed on Oct. 8, 2004.

(51) Int. Cl.
*C12Q 1/68* (2006.01)
*C12P 19/34* (2006.01)
*C07H 21/04* (2006.01)
(52) U.S. Cl. .................. 435/6; 435/91.2; 536/23.1; 536/24.31; 536/24.33
(58) Field of Classification Search ................. None
See application file for complete search history.

(56) References Cited
U.S. PATENT DOCUMENTS

| | | | | |
|---|---|---|---|---|
| 5,582,989 | A * | 12/1996 | Caskey et al. | 435/6 |
| 6,358,679 | B1 * | 3/2002 | Heid et al. | 435/5 |
| 2003/0118998 | A1 * | 6/2003 | Dean et al. | 435/6 |

OTHER PUBLICATIONS

Woischnik et al. Pattern of Organization of Human Mitochondrial Pseudogenes in the Nuclear Genome. Genome Research (2002) 12: 885-893.*
Buck et al. Design strategies and performance of custom DNA sequencing primers. Biotechniques (1999) 27(3): 528-536.*
Haas-Rochholz et al. Additional primer sets for an amelogenin gene PCR-based DNA-sex test. International Journal of Legal Medicine (1997) 110: 312-315.*
Carey et al. Trends in DNA forensic analysis. Electrophoresis (2002) 23: 1386-1397.*
GenBank Accession No. AC010722 (2000). 50 printed pages. Accessed Aug. 29, 2006.*
GenBank Accession No. AC004388 (1998). 65 printed pages. Accessed Aug. 29, 2006.*
Arnason et al. Comparison between the complete mitochondrial DNA sequences of *Homo* and the common chimpanzee based on nonchimeric sequences. Journal of Molecular Evolution (1996) 42: 145-152.*
GenBank Accession No. J01415 (2006). 32 printed pages including revision history. Accessed Aug. 29, 2006.*
William E. Frank et al., "Validation of the AmpFϕSTR™ Profiler Plus PCR Amplification Kit for Use in Forensic Casework", J Forensic Sci 2001; 46(3):pp. 642-646.
Daniel Bogenhagen et al., "The Number of Mitochondrial Deoxyribonucleic Acid Genomes in Mouse L and Human HeLa Cells", The Journal of Biological Chemistry, vol. 249, No. 24, Issue of Dec. 25, pp. 7991-7995, 1974.
John C. Fox et al., Development, Characterization, and Validation of a Sensitive Primate-Specific Quantification Assay for Forensic Analysis, BioTechniques 34: pp. 314-322 (Feb. 2003).
Janice A. Nicklas et al., "Development of an *Alu*-based, Real-Time PCR Method for Quantitation of Human DNA in Forensic Samples", J Forensic Sci, Sep. 2003, vol. 48, No. 5, pp. 936-944.
Melanie E. Sifis et al., "A More Sensitive Method for the Quantitation of Genomic DNA by *Alu* Amplification", J Forensic Sci 2002; 47(3):pp. 589-592.
Jerilyn A. Waker et al., "Human DNA quantitation using *Alu* element-based polymerase chain reaction", Analytical Biochemistry, 315 (2003), pp. 122-128.
Janice A. Nicklas et al., "Development of an *Alu*-Based, QSY 7-Labeled Primer PCR Method for Quantitation of Human DNA in Forensic Samples", J Forensic Sci, Mar. 2003, vol. 48, No. 2, pp. 282-291.
Antonio Alonso et al., "Real-time PCR designs to estimate nuclear and mitochondrial DNA copy number in forensic and ancient DNA studies", Forensic Science International 139 (2004), pp. 141-149.
Hanna Andreasson et al., "Real-Time DNA Quantification of Nuclear and Mitochondrial DNA in Forensic Analysis", BioTechniques 33: pp. 402-411 (Aug. 2002).
Akane et al., Forensic Science International (1992) 52(2): 143-148.

* cited by examiner

*Primary Examiner*—Kenneth R. Horlick
*Assistant Examiner*—Angela Bertagna
(74) *Attorney, Agent, or Firm*—Robert E. Bushnessl, Esq.

(57) ABSTRACT

A comprehensive set of human specific, target specific, multiplex PCR assays for DNA quantitation is provided. Our duplex qPCR for nDNA/mtDNA had a linear quantitation range of 100 ng to 1 pg, and our triplex qPCR assay for nDNA/mtDNA/male Y DNA had a linear range of 100 ng to 0.1 ng. Human-specificity was demonstrated by the accurate detection of 0.05% and 5% human DNA, respectively, from a complex source of starting templates. Target-specificity was confirmed by the lack of cross-amplification among targets. A high throughput alternative for human gender determination was also developed by multiplexing the male Y primer/probe set with an X chromosome based system. Background cross-amplification with DNA templates derived from fourteen other species was negligible aside from the male Y assay which produced spurious amplifications from other non-human primate templates. Mainstream application of these assays will undoubtedly benefit forensic genomics.

37 Claims, 8 Drawing Sheets

FIG. 1

```
AluY    (SEQ ID NO: 1) GAACCCGGGAGGCGGAGCTTGCAGTGAGCCGAGATCGCGCCactgcaCtc   250
AluYb8  (SEQ ID NO: 2) .........A....................T...........g..          250

AluY    (SEQ ID NO: 1) cA-------gcctGGGCGACAGAGCGAGACTCCGTCTCAAAAAA            287
AluYb8  (SEQ ID NO: 2) .gcagtccg...................................          294
```

X-chromosome (SEQ ID NO: 8) AATTTAAAAGGAGGTGTCATCCCCTGTATTTGTTCACTGAAAGAGTCCACGAA
Y-chromosome (SEQ ID NO: 9) AATTTAAAAGGAGGTGTCATCCCCTGTATTTGTTCACTGAGGAGTCCACAAA X-chromosome (SEQ ID NO: 8) CTTTAAATTAGTCACCTACTGCCcagacaatgtg------------------
Y-chromosome (SEQ ID NO: 9) CTTTAAATTAGTCACCTACTGCCAGACAACAATGTGCtaggctctaggaatta X-chromosome (SEQ ID NO: 8) ------------------------------------------------
Y-chromosome (SEQ ID NO: 9) caaaaGAGAGTATGAACAAACTGGCCCTCTTTGAGCCATGCCAGACACT X-chromosome (SEQ ID NO: 8) ------------------------------------------------
Y-chromosome (SEQ ID NO: 9) CTTATAGATCTAGGATGTGATTGAATGTAAATTGAACATAACATAATGG X-chromosome (SEQ ID NO: 8) AGAGAGGAATTAAATTTTGTTAAGAGGTTGAGAAGAGGTTCATAAAGGAG
Y-chromosome (SEQ ID NO: 9) AGAGAGGAATTAAATTTTGTTAAGAGGTTGAGAAGAGGTTCATAAAGGAG

MULTIPLEX PCR FOR SIMULTANEOUS QUANTITATION OF HUMAN NUCLEAR, MITOCHONDRIAL, AND MALE Y-CHROMOSOME DNA

CLAIM OF PRIORITY

This application makes reference to, incorporates the same herein, and claims all benefits accruing under 35 U.S.C. §119 from a provisional application for MULTIPLEX PCR FOR SIMULTANEOUS QUANTITATION OF HUMAN NUCLEAR, MITOCHONDRIAL, AND MALE Y-CHOROMOSOME DNA earlier filed in the United States Patent & Trademark Office on 8 Oct. 2004 and there duly assigned Ser. No. 60/616,852.

GOVERNMENT SUPPORT

This invention was made with government support under grant numbers EPS-0346411 (M.A.B.) sponsored by the National Science Foundation.

BACKGROUND OF INVENTION

1. Field of Invention

The present invention relates to polymerase chain reaction (PCR) assays for a quantitation of human DNA, and more particularly multiplex PCR for simultaneous quantitation of human nuclear, mitochondrial, and male Y-chromosome DNA.

2. Description Of the Related Art

Forensic DNA specimens are commonly matched to alleged criminal suspects in modern law enforcement using human identification systems validated according to the DNA Advisory Board's (DAB) Quality Assurance Standards. These DNA testing systems typically involve the amplification of highly polymorphic short tandem repeats (STR's) by polymerase chain reaction (PCR). AmpF/STR® Profiler Plus and COfiler®, Powerplex®, Powerplex-Y, and Y-PLEX™ 12 are examples of commonly used multiplex systems for genotyping polymorphic STRs residing in the human nuclear (nDNA) and male Y-chromosome DNA. In general, these systems require about 0.1 to 2.0 ng of DNA template for analysis (W. E. Frank et al., J Forensic Sci 46 (2001) 642-646). When DNA evidence is limited, analysis of human mitochondrial DNA (mtDNA) targets is often employed because of the high copy number of mitochondria and mtDNA molecules in each cell (D. Bogenhagen et al., J Biol Chem 249 (1974) 7991-7995). In some cases, DNA evidence obtained from criminal investigations or forensic anthropology studies may be degraded and/or contain non-human contaminants. Consequently, an essential precursor to standard forensic analyses is the sensitive quantitation of human nuclear, mitochondrial, and male Y-chromosome DNA from complex biomaterials.

Commercially available products for human DNA quantitation include AluQuant (Promega Corp.), Quantifiler™ human and Quantifiler™ Y (Applied Biosystems, Inc.). In addition, several real-time PCR assays have been reported for nDNA quantitation (J. C. Fox et al., Biotechniques 34 (2003) 314-322, J. A. Nicklas et al., J Forensic Sci 48 (2003) 936-944, E. Sifis et al., J Forensic Sci 47 (2002) 589-592, J. A. Walker et al., Anal Biochem 315 (2003) 122-128, J. A. Nicklas et al., J. Forensic Sci. 48 (2003) 282-291,) and for the simultaneous quantitation of nDNA and mtDNA (A. Alonso et al., Forensic Science International 139 (2004) 141-149, and H. Andreasson et al., Biotechniques 33 (2002) 402-411).

There are limitations to these previously reported methods. Many of these systems are not human specific and amplify both human and non-human primate DNA (J. C. Fox et al., Biotechniques 34 (2003) 314-322, J. A. Nicklas et al., J Forensic Sci 48 (2003) 936-944, M. E. Sifis et al., J Forensic Sci 47 (2002) 589-592, J. A. Nicklas et al., J. Forensic Sci. 48 (2003) 282-291, and H. Andreasson et al., Biotechniques 33 (2002) 402-411). Some methods are not target specific in that the mtDNA assay also amplifies a product from the nuclear genome (H. Andreasson et al., Biotechniques 33 (2002) 402-411), or is designed in the hyper-variable region (HV) of the mitochondrial genome rather than in the conserved region, thereby increasing the probability of target mismatches and inaccurate quantitation (A. Alonso et al., Forensic Science International 139 (2004) 141-149). Most of these systems are not multiplex compatible (Quantifiler™, Quantifier Y, AluQuant) (J. C. Fox et al., Biotechniques 34 (2003) 314-322, J. A. Nicklas et al., J Forensic Sci 48 (2003) 936-944, M. E. Sifis et al., J Forensic Sci 47 (2002) 589-592 and J. A. Walker et al., Anal Biochem 315 (2003) 122-128), resulting in the possible depletion of valuable DNA specimen prior to subsequent analyses. Most importantly, no system is currently available that meets all of these criteria, human specificity, target specificity, high sensitivity and multiplex compatible.

SUMMARY OF INVENTION

It is therefore an object of the present invention to provide a comprehensive set of human specific, target specific, multiplex PCR assays for DNA quantitation.

It is another object of the present invention to provide primers adapted for a multiplex PCR assays for DNA quantitation.

According to an embodiment of the present invention, a process for quantitating a human nuclear DNA and a human mitochondrial DNA in a sample, the process comprising the steps of: performing multiplex polymerase chain reaction to amplify first genomic DNA containing a human nuclear specific sequence by using a first primer pair and to amplify second genomic DNA containing a human mitochondrial specific sequence by using a second primer pair; and quantitating the human nuclear DNA and the human mitochondrial DNA by comparing the amplified first and second genomic DNA with a reference. It is preferred that the first primer pair specific for human nuclear DNA comprises the following sequences: 5' CTTGCAGTGAGCCGAGATT 3' (SEQ ID NO: 13); and 5' GAGACGGAGTCTCGCTCTGTC 3' (SEQ ID NO: 14). It is preferred that the second primer pair specific for human mitochondrial DNA comprises the following sequences: 5' AATATTAAACACAAACTACCACCTACCT 3' (SEQ ID NO: 10); and 5' TGGTTCTCAGGGTTTGT-TATAA 3' (SEQ ID NO: 11). It is preferred that the quantitation step comprises using a first nucleotide probe containing the following sequence to determine the first genomic human nuclear DNA: 5'ACTGCAGTCCGCAGTCCGGCCT3' (SEQ ID NO: 15), more preferably 5'VIC ACTGCAGTCCG-CAGTCCGGCCT3' MGBNFQ (5'VIC-SEQ ID NO:15-3'MGBNFQ. It is preferred that the quantitation step comprises using a second nucleotide probe containing the following sequence to determine the second genomic human mitochondrial DNA: 5' CCTCACCAAAGCCCATA 3' (SEQ ID NO: 12), more preferably 5' FAM CCTCACCAAAGC-CCATA 3'MGBNFQ (5'FAM-SEQ ID NO:12-3'MGBNFQ).

According to an embodiment of the present invention, primers adapted for a duplex nDNA/mtDNA quantitative assay, said primers comprising: a first primer pair comprising: 5' CTTGCAGTGAGCCGAGATT 3' (SEQ ID NO: 13); and 5' GAGACGGAGTCTCGCTCTGTC 3' (SEQ ID NO: 14); and a second primer pair comprising: .5' AATATTAAACA-CAAACTACCACCTACCT 3' (SEQ ID NO: 10); and 5' TGGTTCTCAGGGTTTGTTATAA 3' (SEQ ID NO: 11).

According to an embodiment of the present invention, a process for quantitating a human nuclear DNA, a human mitochondrial DNA and a human male Y DNA in a sample, said process comprising the steps of: performing multiplex polymerase chain reaction to amplify genomic DNA containing a human nuclear specific sequence by using a first primer pair, to amplify genomic DNA containing a human mitochondrial specific sequence by using a second primer pair, and to amplify genomic DNA containing a human male chromosome specific sequence by using a third primer pair; and quantitating the human nuclear DNA, the human mitochondrial DNA and the human male Y DNA by comparing the amplified products with a reference. It is preferred that the first primer pair specific for human nuclear DNA comprises the following sequences: 5' CTTGCAGTGAGCCGAGATT 3' (SEQ ID NO: 13); and 5' GAGACGGAGTCTCGCTCTGTC 3' (SEQ ID NO: 14). It is preferred that the second primer pair specific for human mitochondrial DNA comprises the following sequences: 5' AATATTAAACACAAAC-TACCACCTACCT 3' (SEQ ID NO: 10); and 5' TGGTTCT-CAGGGTTTGTTATAA 3' (SEQ ID NO: 11). It is also preferred that the third primer pair specific for human male Y DNA comprises the following sequences: 5' CACCTACTGT-GCCAGACAATGTG 3' (SEQ ID NO: 16); and 5' CCCAT-GCCATGTTTGTCATACT 3' (SEQ ID NO: 17).

According to an embodiment of the present invention, a process for quantitating X and Y chromosome in a sample, said process comprising the steps of: performing duplex polymerase chain reaction to amplify genomic DNA containing a human Y chromosome specific sequence by using a third primer pair and to amplify genomic DNA containing a human X chromosome specific sequence by using a fourth primer pair; and quantitating the human Y DNA and the human X DNA by comparing the amplified products with a reference.

It is preferred that the third primer pair specific for human male Y chromosome comprises the following sequences: 5' CACCTACTGTGCCAGACAATGTG 3' (SEQ ID NO: 16); and 5' CCCATGCCATGTTTGTCATACT 3' (SEQ ID NO: 17), and that the fourth primer pair specific for human X chromosome comprises the following sequences: 5' CCAC-GAACTTTAATTAGTCACCTACTGT 3' (SEQ ID NO: 19); and 5' ATTCCTCTCTCCATTATGTTCAATTACA 3' (SEQ ID NO: 20).

According to an embodiment of the present invention, a process for quantitating at least one of a human nuclear DNA, a human mitochondrial DNA, a human Y DNA, and a human X DNA, said process comprising: performing polymerase chain reaction by using at least one of a first primer pair for amplifying first genomic DNA containing a human nuclear specific sequence, a second primer pair for amplifying second genomic DNA containing a human mitochondria specific sequence, a third primer pair for amplifying third genomic DNA containing a human male chromosome specific sequence, and a fourth primer pair for amplifying fourth genomic DNA; and quantitating said at least one of the human nuclear DNA, the human mitochondrial DNA, the human Y DNA and the human X DNA by comparing said at least one of the amplified first, second, third and fourth genomic DNA with a reference.

BRIEF DESCRIPTION OF THE DRAWINGS

A more complete appreciation of the present invention, and many of the above and other features and advantages of the present invention, will be readily apparent as the same becomes better understood by reference to the following detailed description when considered in conjunction with the accompanying drawings in which like reference symbols indicate the same or similar components, wherein:

FIG. 1 shows a sequence alignment of a portion of the Alu Y and Yb8 consensus sequences used in the design of the nDNA quantitation assay according to an embodiment of the present invention;

FIG. 2 shows a sequence alignment of a part of the human mitochondrial consensus sequence;

FIG. 3 shows a sequence alignment of a portion of the homologous region of the human sex chromosomes;

DESCRIPTION OF THE PREFERRED EMBODIMENTS

Figure 4A:
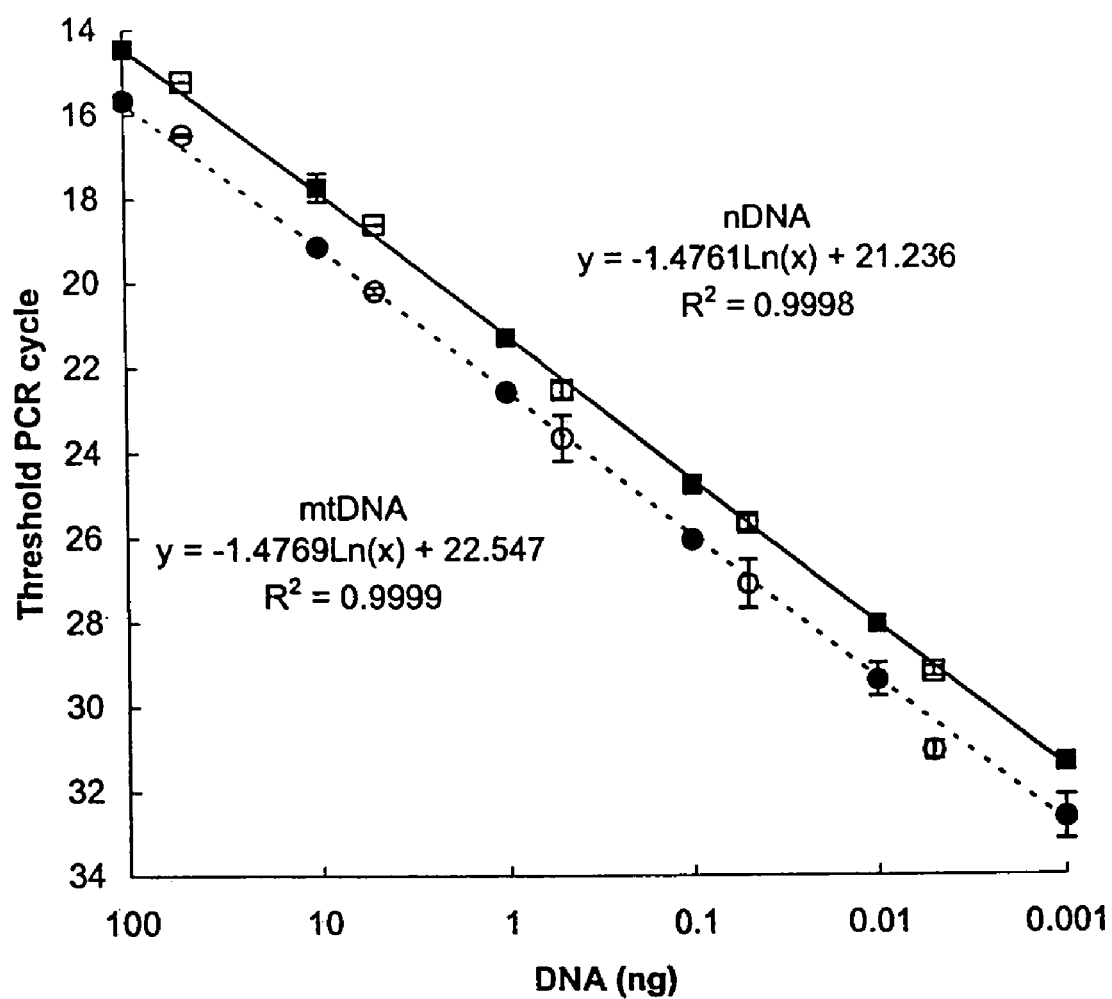
FIG. 4A is a graph showing an effective quantitation range of the nDNA/mtDNA duplex PCR assay using TaqMan-MGB probes according to an embodiment of the present invention.

To overcome the limitations associated with previously reported methods for human DNA quantitation, we have used a systematic approach to the design and implementation of a comprehensive set of multiplex PCR assays for the rapid detection and quantitation of human DNA using TaqMan-MGB probes. These include, but are not limited to, a duplex quantitative PCR (qPCR) assay for human nDNA and mtDNA, the first triplex qPCR assay for the simultaneous quantitation of human nDNA, mtDNA, and male Y chromosome DNA, and a duplex PCR assay for human sex typing.

The human nuclear DNA quantification assay is an intra-Alu based design incorporating the 7 bp duplicated region characteristic of the Yb-lineage of Alu subfamilies and an AluYb8 diagnostic base at the 3' end of the forward primer. FIG. 1 shows sequence alignment of a portion of the Alu Y and Yb8 consensus sequences used in the design of our nDNA quantitation assay. The dots represent the same nucleotide as the ancestral Alu Y consensus sequence. Deletions are shown as dashes and the subfamily diagnostic mutations are shown as the correct base. The intra-AluYb8 oligonucleotide primers are shown in boldface and the TaqMan-MGB probe labeled with 5' VIC is shown in small letter underlined font.

Figure 2:
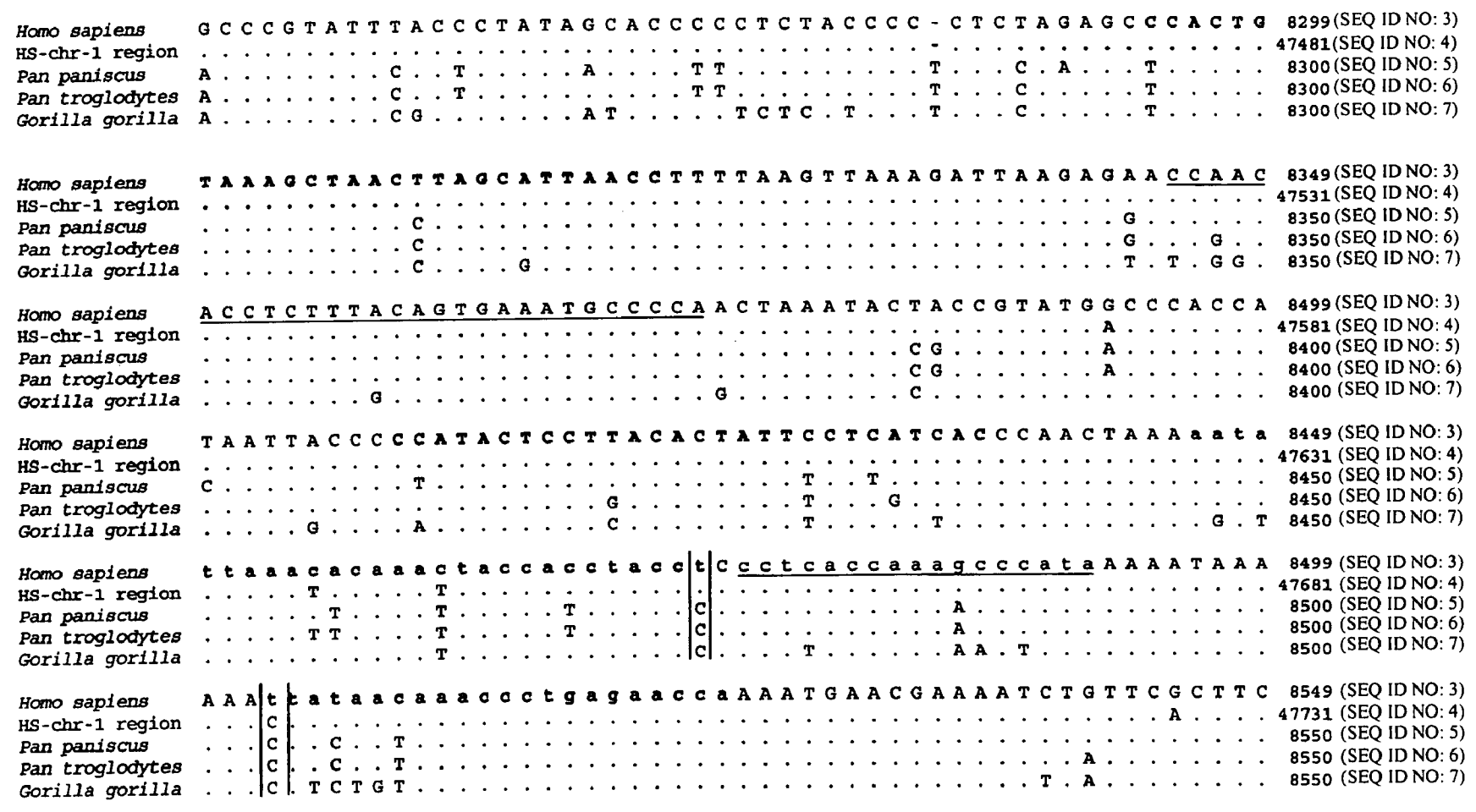

Our human specific mitochondrial assay was designed to incorporate human/chimp mismatches at the 3' ends of each primer and a single mtDNA/nuclear DNA mismatch at the 3' end of the reverse primer. FIG. 2 shows sequence alignment of a part of the human mitochondrial consensus sequence. The alignment shows position 8250 to 8550 of human mtDNA, aligned for comparison with non-human primate mtDNA consensus sequences and a target from the human nuclear genome with 98% sequence similarity to the human mtDNA consensus sequence. The dots represent the same nucleotide as the human consensus sequence. Deletions are shown as dashes and mutations are shown as the correct base. A previously reported assay (H. Andreasson et al., Biotechniques 33 (2002) 402-411) has primers in bold upper case (mt-8294F and mt-8436R) and probe (mt-8345) in underlined upper case, while our design has primers in bold small letter (mt-8446F and mt-8525R) and probe (mt-8475) in underlined lower case.

The sex chromosome assays were designed around a 90 bp deletion on the human X-chromosome in the X-Y homologous region. In FIG. 3, primers are shown in bold font and the chromosome specific probes are shown in lower case underlined font. The deletion starts at X position 89810740 as determined by BLAT (The BLAST like Alignment Tool). Forward primer 5'CCACGAACTTTAATTAGTCAC-CTACTGT 3'(SEQ ID NO: 19) and reverse primer 5'ATTC-CTCTCTCCATTATGTTCAATTACA 3'(SEQ ID NO:20) were used to PCR amplify a 77 bp fragment on the human X chromosome and a 167 bp fragment on the human Y chromosome. FIG. 3 shows sequence alignment of a portion of the homologous region of the human sex chromosomes. The dashes represent a 90 bp deletion specific to the human X chromosome. Primers are shown in bold font and the chromosome specific TaqMan-MBG probes are shown in lower case underlined font.

EXAMPLES

Materials and Methods

PCR Primer and Probe Design

Oligonucleotide PCR primers and TaqMan-MGB™ probes were designed using Primer Express software (Applied Biosystems, Inc.). Primers were purchased from Sigma-Genosys, Inc. and probes were purchased from Applied Biosystems, Inc (Table 1). Each primer pair was evaluated in our laboratory using standard agarose gel electrophoresis prior to the purchase of the probes.

TABLE 1

Oligonucleotide primers and probes for human DNA quantitation assays

| Assay | Forward Primer Reverse Primer | Probe | Size (bp) |
|---|---|---|---|
| mtDNA | 5'AATATTAAACACAAACTACC ACCTACCT3' (SEQ ID NO:10) 5'TGGTTCTCAGGGTTTGTTAT AA3' (SEQ ID NO:11) | 5'FAM CCTCACCAAAGCCCATA3' MGBNFQ (SEQ ID NO:12) | 79 |
| nDNA | 5'CTTGCAGTGAGCCGAGATT3' (SEQ ID NO:13) 5'GAGACGGAGTCTCGCTCTGT C3' (SEQ ID NO:14) | 5'VICACTGCAGTCCGCAGT CCGGCCT3'MGBNFQ (SEQ ID NO:15) | 71 |
| Y-male | 5'CACCTACTGTGCCAGACAAT GTG3' (SEQ ID NO:16) 5'CCCATGCCATGTTTGTCATA CT3' (SEQ ID NO:17) | 5'NEDTAGGCTCTAGGAAT ACAAAA3'MGBNFQ (SEQ ID NO:18) | 69 |
| X-Chr | 5'CCACGAACTTTAATTAGTCA CCTACTGT3' (SEQ ID NO:19) 5'ATTCCTCTCTCCATTATGTTC AATTACA3' (SEQ ID NO:20) | 5'VICCAGACAATGTGATAA ATG3'MGBNFQ (SEQ ID NO:21) | 77 |

Complete mitochondrial genome sequences were downloaded from the University of Montreal website. Human sequence was selected from 36 different *Homo sapiens* accession loci and aligned using MegAlign with the ClustalW algorithm and the default settings (DNAstar Version 5.0 for Windows) to obtain a human consensus sequence in the conserved region of the mitochondrial genome. Next, sequences from pygmy chimpanzee (*Pan paniscus*, n=1), common chimpanzee (*Pan troglodytes*, nz=2), and Gorilla (*Gorilla gorilla*, n=2) were aligned with the human consensus sequence to determine regions that were human specific. Lastly, sequence from a region of human chromosome 1 nearly identical to the mitochondrial sequence (*Homo sapiens* chromosome 1 genomic contig gi|129791381|ref|NT_034471.3|Hs1$_{13}$34633[29791381]) was downloaded from the National Center for Biotechnology Information and aligned with the previous mitochondrial genome sequences. A consensus alignment of these data is shown in FIG. 2, comparing a previously reported assay (H. Andreasson, U. Gyllensten, and M. Allen, Real-time DNA quantification of nuclear and mitochondrial DNA in forensic analysis, Biotechniques 33 (2002) 402-411) to our design. Our human specific mitochondrial assay was designed to incorporate human /chimp mismatches at the 3' ends of each primer and a single mtDNA /nuclear DNA mismatch at the 3' end of the reverse primer (FIG. 2).

The sex chromosome assays were designed around a 90 bp deletion on the human X-chromosome in the X-Y homologous region (FIG. 3). Primers are shown in bold font and the chromosome specific probes are shown in lower case underlined font. The deletion starts at X position 89810740 as determined by BLAT (The BLAST like Alignment Tool). This X-deletion is being reported here for the first time. We tested the locus for fixation and human gender identification in 593 diverse humans of known gender (Table 2) with 100% accuracy. The DNA sample set contained individuals from different geographic origins to control for possible population-specific mutations that might impact the amplification of the locus. Of the 593 DNA samples tested, 545 were obtained from paternity/identity cases and the remaining samples were purchased from Coriell Cell Repositories (Camden, N.J.). The forward primer 5'CCACGAACTTTAATTAGTCAC-CTACTGT 3'(SEQ ID NO:19) and the reverse primer 5'ATTCCTCTCTCCATTATGTTCAATTACA 3'(SEQ ID NO:20) were used to PCR amplify a 77 bp fragment on the human X chromosome and a 167 bp fragment on the human Y chromosome and products were resolved on a 2% agarose gel stained with ethidium bromide.

TABLE 1

DNA samples to tested for gender identification

| Population | Males | Females | Total |
|---|---|---|---|
| Africa-American | 150 | 141 | 291 |
| European-American | 49 | 60 | 109 |
| Hispanic-American | 9 | 7 | 16 |
| North American | 75 | 54 | 129 |
| South American | 7 | 12 | 19 |
| Asian | 15 | 14 | 29 |
| Total | 305 | 288 | 593 |

PCR Amplification

Quantitative PCR experiments were performed using an ABI Prism 7000 sequence detection system and TaqMan™ PCR core reagents (kit #4304439) from Applied Biosystems, Inc. Universal PCR cycling conditions consisted of an initial 2 minutes at 50° C. for activation of the AmpErase® UNG, followed by a denaturation step of 10 minutes at 95° C. to activate the AmpliTaq Gold®, and then 40 amplification cycles of denaturation at 95° C. for 15 seconds and one minute of anneal/extension at 60° C. Each quantitative PCR reaction contained 45 µl of PCR master mix and 5 µl of DNA template and were carried out in 50 µl using 1× TaqMan buffer and 0.5 units AmpErase® UNG as recommended by the supplier. Other reagents were optimized as follows. The duplex nDNA/mtDNA quantitative assay used 1 µM primers, 100 nM of each probe, 0.5 mM dNTP's, 5.0 mM $MgCl_2$ and 2.5 units AmpliTaq Gold® DNA polymerase. The triplex nDNA/mtDNA/male Y assay used 100 nM nDNA primers, 600 nM mtDNA primers, 1 µM male Y primers, 100 nM nDNA and mtDNA probes and 250 nM male Y probe, 0.2 mM dNTPs, 3.0 mM $MgCl_2$ and 1.25 units AmpliTaq Gold® DNA polymerase. The duplex X/Y assay used 1 µM X-chromosome primers, 200 nM male Y-chromosome primers, 100 nM each probe, 0.2 mM dNTP's, 5.0 mM $MgCl_2$ and 1.25 units AmpliTaq Gold® DNA polymerase.

DNA Samples

Human DNA standards were isolated from the HeLa cell line (ATCC CCL2; American Type Culture Collection, Manassas, Va.) using Wizard genomic DNA purification (Promega Corporation, Madison, Wis.). Extracted DNA was stored in 10 mM Tris/0.1 mM EDTA (TLE), quantified spectrophotometrically and then serially diluted 10-fold in TLE such that concentrations from 100 ng to 0.01 pg were assayed in duplicate using PCR. Human male DNA standards (NA17055 and NA17316) were purchased from Coriell Cell Repositories (Camden, N.J.) and serially diluted as above. Human nuclear DNA was obtained from a human-rodent somatic cell hybrid panel from the NIGMS Human Genetic Mutant Cell Repository at Coriell Institute, Camden, N.J. (panel 2). DNA from pygmy chimpanzee (*Pan paniscus*; NG05253), common chimpanzee (*Pan troglodytes*; NG06939), and gorilla (*Gorilla gorilla*; NG05251) were purchased from Coriell Cell Repositories. DNA from dog (*Canis familiaris*), cat (*Felis catus*), rabbit (*Oryctolagus cuniculus*), cow (*Bos taurus*), horse (*Equus caballus*), and sheep (*Ovis aries*) were obtained by tissue and blood extraction using the Wizard Genomic DNA Purification kit (Promega Corporation, Madison, Wis.) and samples provided by the Louisiana State University School of Veterinary Medicine. DNA from pig (*Sus scrofa*), deer (*Odocoileus virginianus*), rat (*Rattus norvegicus*), and mouse (*Mus musculus*) were prepared from tissue with proteinase K digestion followed by phenol:chloroform extraction and ethanol precipitation (W. M. Strauss, in: W. M. Ausubel (Ed.), *Current Protocols in Molecular Biology*, Wiley, New York, 1998, pp. 2.2.1-2.2.3). Chicken (*Gallus gallus*) DNA was extracted from blood using the QIAamp DNA blood mini kit® (QIAGEN, Inc., Valencia, Calif.).

Data Analysis

Separate standard curves were constructed for each component of the multiplex quantitative assays as follows. Data from duplicate human DNA standards were exported from the ABI Prism 7000 SDS software® into a Microsoft Excel spreadsheet where the mean value and standard deviation were calculated for each point on the standard curve. Using the Excel trendline option, a line of best fit was plotted with Y-error bars equal to one standard deviation to form a standard curve. Data from the negative control (no template control—NTC) duplicates and the "domestic DNA mixture" test samples (Table 3) (mean+/−one standard deviation of duplicates) were then plotted on the graph for comparison to the standard curve. Pairwise t-tests were performed to determine if the NTC for each assay was statistically different from the minimum value on the standard curve ($p \leq 0.05$).

Data from the multi-species cross-amplification experiments were exported to Excel in a similar manner and the mean and standard deviation of duplicates were calculated. The Excel chart wizard was used to construct bar graphs with Y-error bars equal to one standard deviation.

TABLE 3

Compositions of mixed-DNA test samples

| Contents Mix | Human male | | Dog | | Cat | | Total template | |
|---|---|---|---|---|---|---|---|---|
| | DNA (ng) | % | DNA (ng) | % | DNA (ng) | % | DNA (ng) | % |
| 1 | 50 | 50 | 25 | 25 | 25 | 25 | 100 | 100 |
| 2 | 5 | 50 | 2.5 | 25 | 2.5 | 25 | 10 | 100 |
| 3 | 0.5 | 5 | 5 | 50 | 4.5 | 45 | 10 | 100 |
| 4 | 0.05 | 0.5 | 5 | 50 | 4.95 | 49.5 | 10 | 100 |
| 5 | 0.005 | 0.05 | 5 | 50 | 4.995 | 49.95 | 10 | 100 |

Results

The present invention is a comprehensive set of human specific, target specific, multiplex PCR assays using TaqMan-MGB fluorescent labeled probes, including the first reported triplex assay for the simultaneous detection and quantitation of human nDNA, mtDNA, and male Y DNA in a single reaction.

The nuclear target in this multiplex quantification system is an intra-Alu PCR assay designed within the largely human specific subfamily of AluYb8 elements (FIG. 1). There are about 1800 copies of the Alu Yb-lineage elements in the human genome (A. B. Carter et al., Human Genomics 1 (2004) 167-178, which is incorporated herein by reference).

Assay specificity also dictated our design of a mitochondrial DNA target. The human genome project revealed that transfer of large mitochondrial fragments to the nucleus is a continuous evolutionary process and that essentially all parts of the human mitochondrial genome are represented somewhere in the nuclear genome (T. Mourier, A. J. Hansen, E. Willerslev, and P. Arctander, The Human Genome Project reveals a continuous transfer of large mitochondrial fragments to the nucleus, Mol Biol Evol 18 (2001) 1833-1837). We used analysis of existing DNA sequence databases to facilitate a large scale comparison between the human mitochondrial genome, human nuclear genome, and the mitochondrial genomes of other non-human primates to create a target specific design.

The nDNA/mtDNA duplex qPCR assay had a linear quantitation range of 100-0.001 ng (1 pg), or $10^6$, as shown by the standard curves (FIG. 4A) and was identical to separate monoplex runs of each assay (data not shown). In FIG. 4A, the PCR cycle at which the fluorescent signal crosses baseline is considered to be the threshold cycle, plotted on the y axis. The fluorescent signal produced by a 10-fold dilution series of human DNA is plotted as the mean of duplicates+/−1 standard deviation. The $R^2$ value is 100% for both the nDNA standard curve (solid line with filled squares) and the mtDNA standard curve (dotted line with filled circles). Analyses of DNA mixtures 1-5 outlined in Table 3 are plotted in order as open symbols along each standard curve (squares or circles, respectively) as the mean of duplicates+/−1 standard deviation. Their alignment along each standard curve demonstrates the ability of the duplex assay to simultaneously quantitate human nDNA and mtDNA from within a complex source of starting templates.

Figure 4B:
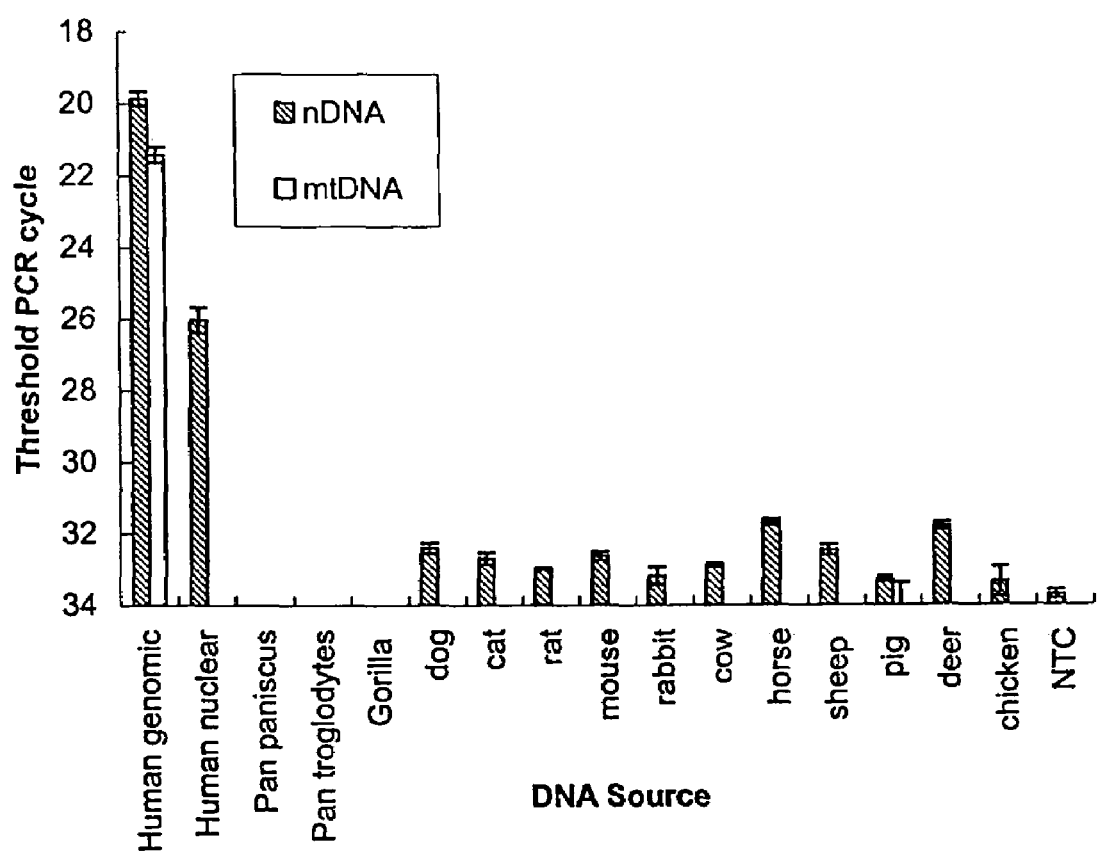
FIG. 4B is a graph showing background amplification of the nDNA/mtDNA duplex PCR assay using TaqMan-MGB probes according to an embodiment of the present invention.

The NTC (no template controls) were detectable below the 1 pg level of 31.3+/−0.01. The mean value of the nDNA NTC was 33.7+/−0.1 (p =0.0282) and the mean value of the mtDNA NTC was 37.1 +/−0.7 (p=0.1238). This duplex assay detected the known values of human DNA from within a "domestic DNA mixture" containing dog and cat DNA from 50% (50 ng and 5 ng) to 0.05% (5 pg) as indicated by the open symbols along each standard curve. The compositions of the various DNA mixtures are shown in Table 3. Background cross-amplification with DNA templates derived from 14 other species, including 3 closely related non-human primate species, was negligible prior to 32 cycles of PCR for the nDNA component and absent for the mtDNA component (FIG. 4B). This further demonstrates that this duplex assay is human specific within its quantitative range. In addition to being human specific, both assay components were target specific in that the nDNA PCR product had no significant sequence identity to any portion of the human mitochondrial genome and the mtDNA assay did not cross-amplify with nDNA targets obtained from a human-rodent somatic cell hybrid panel (FIG. 4B). In FIG. 4B, the PCR cycle at which the fluorescent signal crosses baseline is considered to be the threshold cycle, plotted on the y axis as the mean of duplicate +/−1 standard deviation. Human genomic DNA (2 ng) is compared to human nuclear DNA derived from a human-rodent somatic cell hybrid panel containing no human mtDNA and equal amounts of DNA template from 14 other species, including 3 other primate species. Background cross-species amplification was negligible prior to 32 cycles of PCR for the nDNA component and completely absent in the mtDNA component. This demonstrates that this duplex assay is human specific within its effective quantitative range.

Figure 5A:
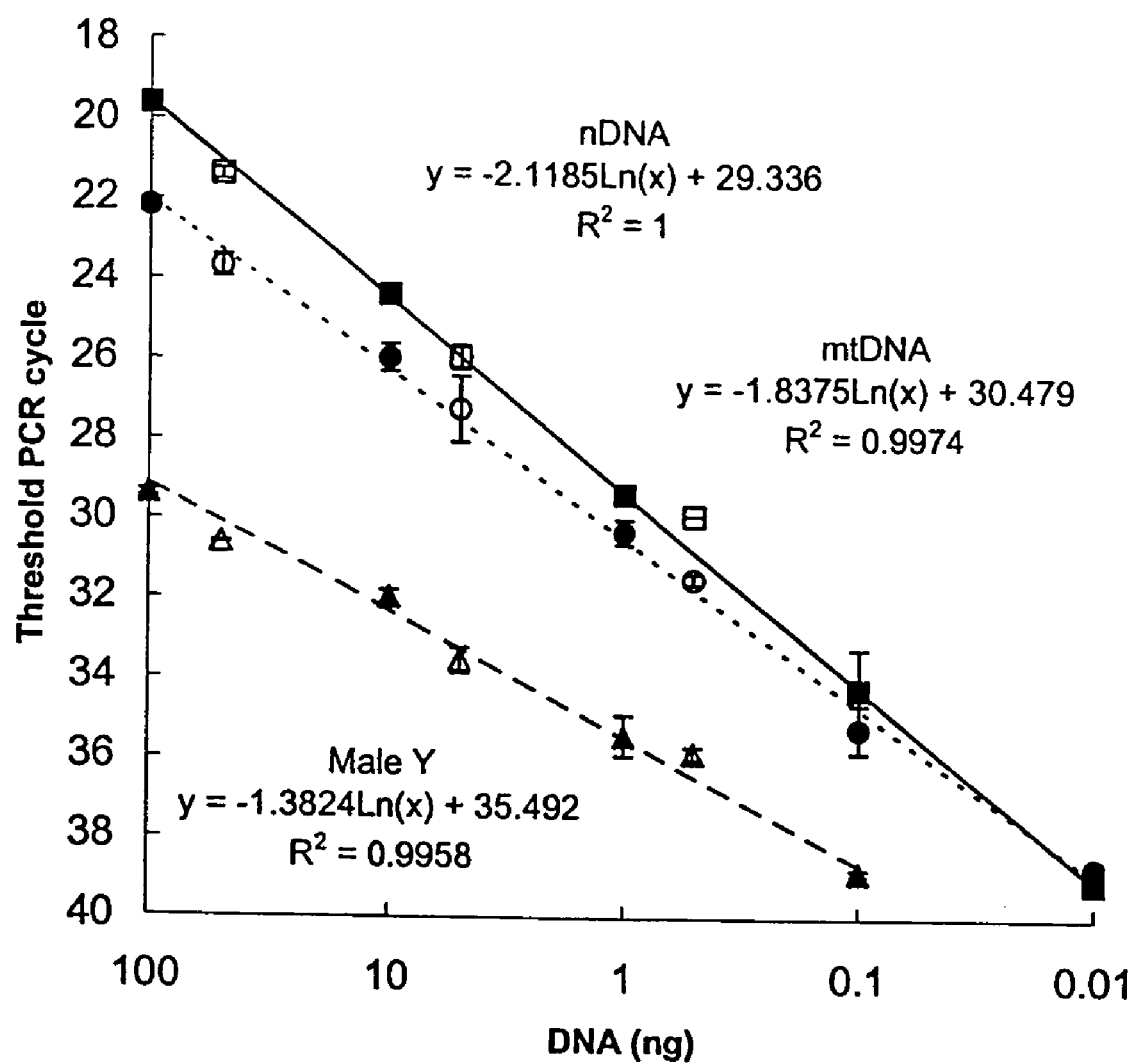
FIG. 5A is a graph showing an effective quantitation range of the triplex PCR assay for the simultaneous quantification of human nDNA, mtDNA and male Y DNA using TaqMan-MGB probes according to an embodiment of the present invention.
Figure 5B:
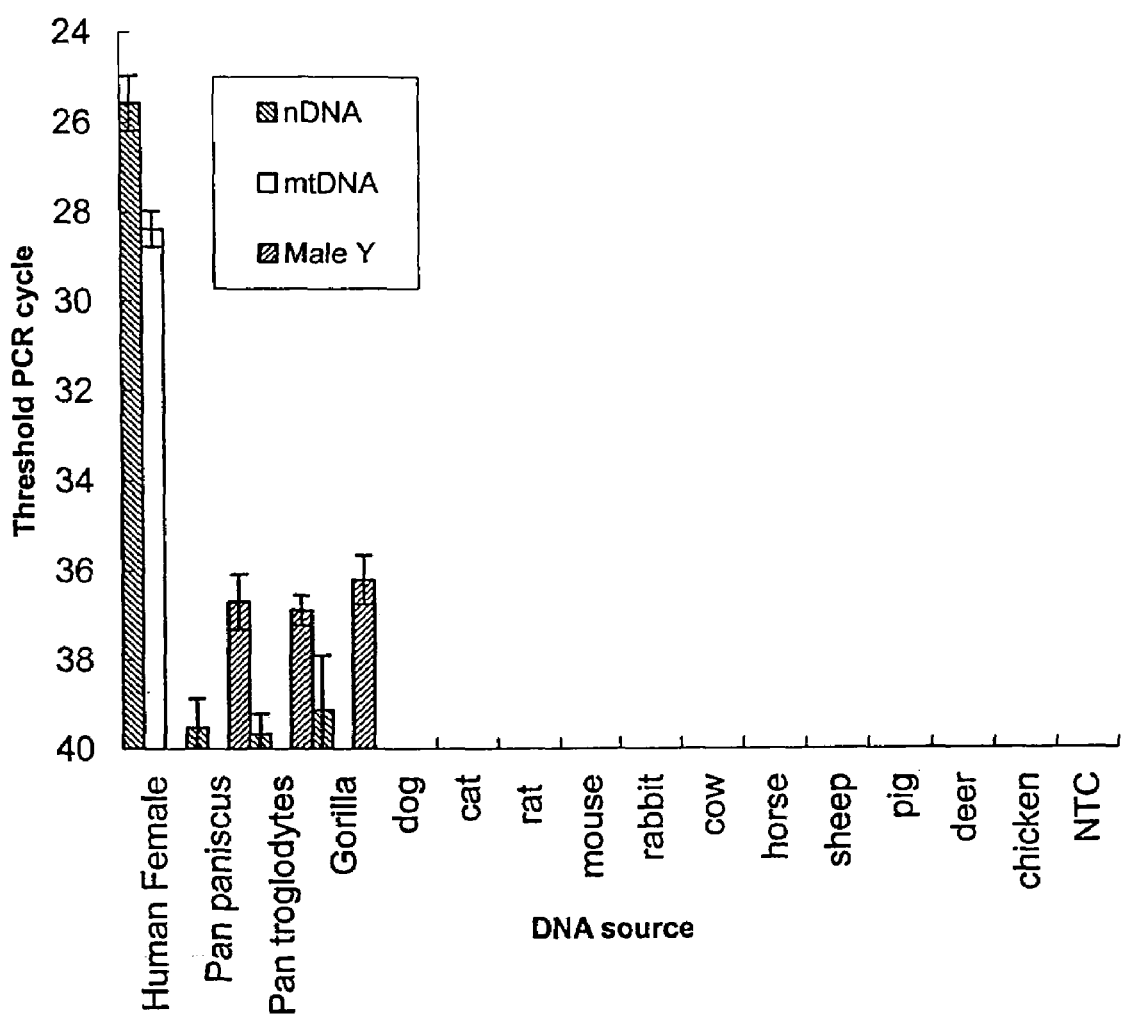
FIG. 5B is a graph showing a background PCR amplification of the triplex PCR assay for the simultaneous quantification of human nDNA, mtDNA and male Y DNA using TaqMan-MGB probes according to an embodiment of the present invention.

The triplex qPCR assay (nDNA, mtDNA, and male Y DNA) had a linear quantitation range of 100-0.1 ng, or $10^4$, as shown by the three standard curves (FIG. 5A). The NTC was not detectable up to 40 cycles of PCR for any of the triplex components. The addition of the male Y locus to the nDNA/mtDNA duplex resulted in reduced assay sensitivity, but quantitative accuracy was maintained as the triplex assay detected from 50% (50 ng and 5 ng) to 5% (0.5 ng) human DNA from the complex mixtures as indicated by the open symbols along each standard curve (FIG. 5A). Background cross-species amplification was negligible prior to 39 cycles of PCR for the nDNA component and absent for the mtDNA component. The male Y component of the triplex exhibited some cross-amplification with DNA templates derived from other primate species only, but since the other two components of the triplex are human specific, the assay is human specific within its quantitative range (FIG. 5B). Cross-amplification among assay targets was still negligible as in the duplex nDNA/mtDNA assay. The male Y assay did not cross-amplify with human female DNA (FIG. 5B).

In FIG. 5A, the PCR cycle at which the fluorescent signal crosses baseline is considered to be the threshold cycle, plotted on the y axis. The fluorescent signal produced by a 10-fold dilution series of human male DNA is plotted as the mean of duplicates+/−1 standard deviation. The $R^2$ value is 99-100% for all three assay components, the nDNA standard curve (solid line with filled squares), the mtDNA standard curve (dotted line with filled circles), and the male Y standard curve (dashed line with filled triangles). Analyses of DNA mixtures 1-3 outlined in Table 3 are plotted in order as open symbols along each standard curve (squares, circles, or triangles, respectively) as the mean of duplicates+/−1 standard deviation. Their alignment along each standard curve demonstrates the ability of the triplex assay to simultaneously quantitate human nDNA, mtDNA and male Y DNA from within a complex source of starting templates. In FIG. 5B, the PCR cycle at which the fluorescent signal crosses baseline is considered to be the threshold cycle, plotted on the y axis as the mean of duplicates+/−1 standard deviation. Human genomic DNA (2 ng) is compared to equal amounts of DNA template from 14 other species, including 3 other primate species. Background cross-species amplification was negligible prior to 39 cycles of PCR for the nDNA component and completely absent for the mtDNA component. The male Y component of the triplex exhibited some cross-amplification within other primate species only.

Figure 6:
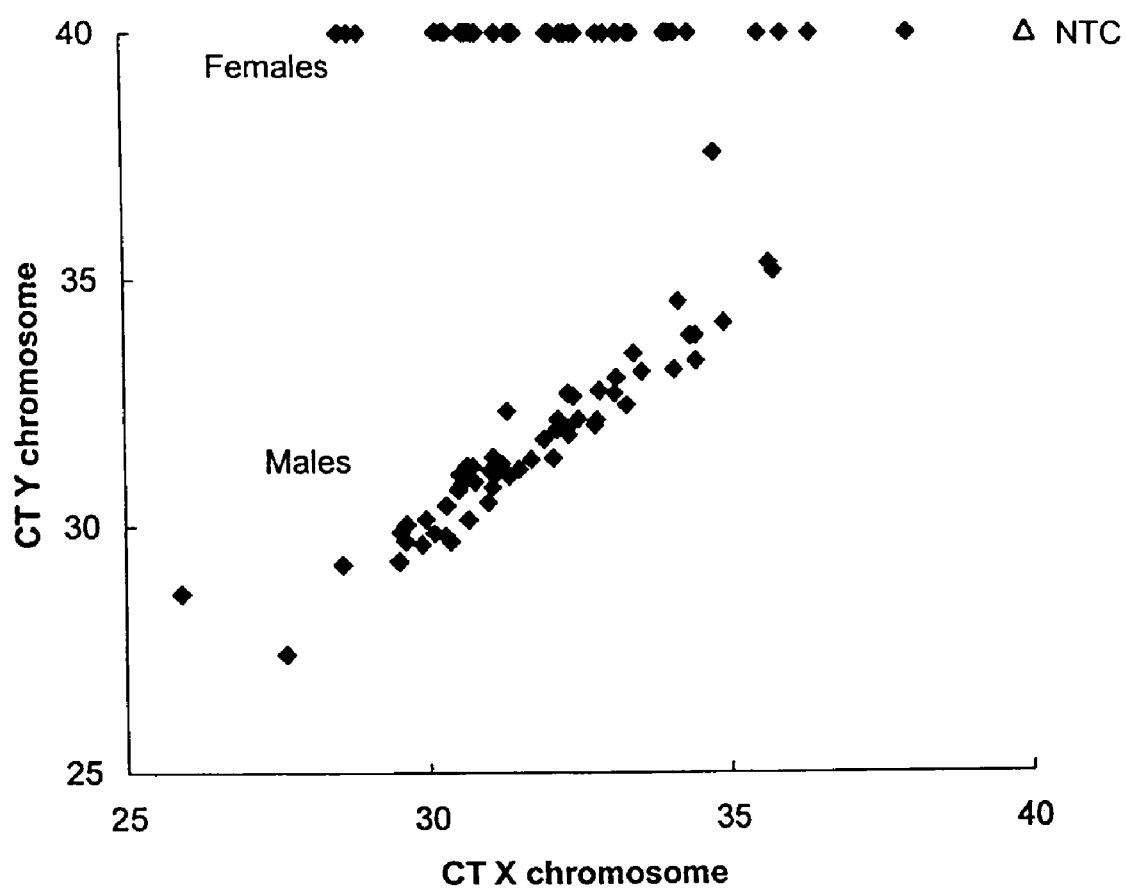
FIG. 6 is a graph for showing the human gender determination using the X/Y duplex PCR assay according to an embodiment of the present invention.

The human sex chromosome X/Y duplex correctly identified the gender of 95 individuals simultaneously on a single PCR plate (FIG. 6). A scatter plot of the threshold PCR cycle data for X (CT X, plotted on the x axis) and male Y (CT Y, plotted on the y axis) illustrates the ability of the duplex to identify gender. The NTC was not detectible up to 40 cycles or PCR. Using a Microsoft excel spread sheet, the data was analyzed to automate gender assignment. In FIG. 6, a scatter plot of the threshold PCR cycles (CT) for X chromosome detection (x axis) and Y chromosome detection (y axis) illustrate the utility of this assay for high through-put human gender identification. Males exhibit fluorescent signal for both sex chromosomes while females exhibit signal only for the X chromosome. The NTC (open triangle) exhibits no signal.

We have designed and evaluated a comprehensive set of human specific multiplex PCR assays for the rapid quantitation of human nuclear, mitochondrial and sex chromosome DNA. Forensic DNA testing typically involves analysis of autosomal STRs, Y-chromosome STRs or mitochondrial DNA sequence determination at the hyper-variable regions 1 and 2 (HV-1 and HV-2). The decision to implement one or more of these approaches is based on several factors, such as the type of evidence, case history, quantity of evidence, supportive evidence, etc. The use of independent assays for human nuclear DNA, human male DNA and mitochondrial DNA leads to consumption of valuable DNA evidence, which is typically available in limited quantity. The multiplex assay, for instance the triplex assay, reported here determines the quantities of DNA template required for all three types of DNA analysis in a single PCR, thereby consuming minimal DNA evidence in the course of determining which type of subsequent analyses should be performed.

Undoubtedly, the triplex assay for simultaneous quantification of human nDNA, mtDNA and male Y DNA in a single PCR reaction is the most efficient and informative of the assays presented here when unknown DNA evidence is being tested. The PCR amplification takes less than 2 hours using universal cycling parameters on an ABI 7000 sequence detection system. Inclusion of human male and female DNA standards in the triplex assay allows for gender determination of unknown samples and also serves as a positive control for samples which do not contain human DNA. The amount of DNA template typically required for STR analyses ranges from 0.1 to 2.0 ng and therefore falls within the linear quantitative range of this triplex PCR assay. Some reduction of PCR amplification efficiency occurs with the triplex compared to the nDNA/mtDNA duplex as noted by the slopes of each standard curve beginning to deviate from 3.33 (100% amplification efficiency of a 10-fold dilution series). The slopes were 4.81, 4.26, and 3.18 for the nDNA, mtDNA, and male Y DNA assay components, respectively. This is not unexpected according to the Applied Biosystems Sequence Detection Systems Chemistry Guide. Multiplex PCR chemistry becomes increasingly more complex as the number of targets increases. The more abundant targets of nDNA and mtDNA had to be primer limited in order to permit efficient amplification of the less abundant male Y target. This phenomenon is not unique to TaqMan based chemistry and is a common obstacle in multiplex assay design. However, the $R^2$ value for each standard curve remained near 100% in the triplex assay, allowing for accurate quantitation of each component simultaneously.

Development of a comprehensive set of human specific multiplex quantitative PCR assays like those reported here, allows investigators to select the most appropriate for the circumstances. If the expected amount of recoverable DNA evidence is below 0.1 ng, then the nDNA/mtDNA duplex assay may be a better choice than the triplex. The 100-fold increase in sensitivity of the duplex (down to 1 pg) may effectively quantitate trace amounts of DNA such that recent advancements in whole genome amplification technology could be employed as a useful strategy (K. J. Sorensen, K. Turteltaub, G. Vrankovich, J. Williams, and A. T. Christian, Whole-genome amplification of DNA from residual cells left by incidental contact, Anal Biochem 324 (2004) 312-314, which is incorporated herein by reference). Also, if the DNA source is known to be female only, then the duplex assay would be more appropriate than the triplex.

If the situation likely involves both male and female DNA, such as in sexual assault cases, X and Y chromosome STR analyses may be typically used to determine if there are multiple contributors and for sorting out the relative contributions of male and female DNA. This may limit the need for an X/Y quantitative assay in typical forensic applications. However, a duplex X/Y quantitation assay may be useful in the detection of rare sex chromosomal disorders such as Klinefelter's syndrome (XXY) and XYY syndrome.

More importantly, this recently discovered human X-chromosome deletion represents an alternative to the use of the *Amelogenin* locus for a high throughput system for human gender determination. Several researchers have recommended that *Amelogenin* not be relied upon as the sole determinant of gender, and this X/Y duplex assay may provide a useful alternative. The PCR amplification takes less than 2 hours using universal cycling parameters on an ABI 7000 sequence detection system and can also be performed as an endpoint assay using a conventional thermal cycler and a fluorescent plate reader. The fact that it is fluorescent based, multiplex compatible and can be automated may make it a useful tool when large scale gender verification is required such as in the Olympic games when several thousand athletes need to be genotyped.

Although similar methods have been reported previously, there are several advantages to our human specific multiplex PCR systems. First, we have designed our assays to meet strict specifications. They must be human specific, target specific and multiplex compatible. The previously reported methods do not meet all three of these criteria. The ability to multiplex the different assays was achieved by using Primer Express universal cycling parameters (Applied Biosystems, Inc.) to design each assay, followed by systematic optimization of PCR reagent concentrations. Assay specificity was achieved by careful comparison of the intended target sequences to other genomes and then systematic evaluation of the assays for cross-amplification. Our male Y assay exhibited some cross-species amplification with DNA derived from other primate species. Since this assay is based on a human X-deletion, other primate species which lack the deletion would be expected to have sequence similar to the human male Y, especially since the sex chromosomes have reduced evolutionary polymorphism rates compared to their autosomal counterparts (P. A. Callinan, D. J. Hedges, A. H. Salem, J. Xing, J. A. Walker, R. K. Garber, W. S. Watkins, M. J. Bamshad, L. B. Jorde, and M. A. Batzer, Comprehensive analysis of Alu-associated diversity on the human sex chromosomes, Gene 317 (2003) 103-110): This was confirmed by a BLAT (BLAST like Alignment Tool) search of the chimpanzee genome using the PCR product used in this study which resulted in a 100% match on the chimpanzee Y chromosome. However, the fact that our male Y assay is used as part of a multiplex, the background amplification signal in other primates does not affect assay specificity. Furthermore, the sequence similarity to other primate genomes can make one fairly certain that this male Y locus is fixed in all human males.

Another advantage to our multiplex qPCR assays is the high copy number target used in our intra-AluYb8 nDNA assay compared to single copy targets used in previous methods (A. Alonso, P. Martin, C. Albarran, P. Garcia, O. Garcia, L. F. de Simon, J. Garcia-Hirschfeld, M. Sancho, C. de la Rua, and J. Fernandez-Piqueras, Real-time PCR designs to estimate nuclear and mitochondrial DNA copy number in forensic and ancient DNA studies, Forensic Science International 139 (2004) 141-149 and H. Andreasson, U. Gyllensten, and M. Allen, Real-time DNA quantification of nuclear and mitochondrial DNA in forensic analysis, Biotechniques 33 (2002) 402-411). The quantitative range of our nDNA assay is $10^6$ with a minimum effective quantitation level of 1 pg of DNA. This exceeds previously reported multiplex compatible nDNA quantitation assays by a minimum of 3-fold (H. Andreasson, U. Gyllensten, and M. Allen, Real-time DNA quantification of nuclear and mitochondrial DNA in forensic analysis, Biotechniques 33 (2002) 402-411) In addition, our PCR assays involve the amplification of smaller PCR products and should be more tolerant of degraded DNA. Our nDNA amplicon is 7 bp (9%) (H. Andreasson, U. Gyllensten, and M. Allen, Real-time DNA quantification of nuclear and mitochondrial DNA in forensic analysis, Biotechniques 33 (2002) 402-411) and 35 bp (33%) (A. Alonso, P. Martin, C. Albarran, P. Garcia, O. Garcia, L. F. de Simon, J. Garcia-Hirschfeld, M. Sancho, C. de la Rua, and J. Fernandez-Piqueras, Real-time PCR designs to estimate nuclear and mitochondrial DNA copy number in forensic and ancient DNA studies, Forensic Science International 139 (2004) 141-149) shorter, our mtDNA amplicon is 63 bp (44%) (H. Andreasson, U. Gyllensten, and M. Allen, Real-time DNA quantification of nuclear and mitochondrial DNA in forensic analysis, Biotechniques 33 (2002) 402-411) and 34 bp (30%) shorter and our X/Y amplicons are 29 bp (27%) and 43 bp (38%) shorter, respectively (A. Alonso, P. Martin, C. Albarran, P. Garcia, O. Garcia, L. F. de Simon, J. Garcia-Hirschfeld, M. Sancho, C. de la Rua, and J. Fernandez-Piqueras, Real-time PCR designs to estimate nuclear and mitochondrial DNA copy number in forensic and ancient DNA studies, Forensic Science International 139 (2004) 141-149).

We have demonstrated that these multiplex PCR assays for the rapid quantitation of human nuclear, mitochondrial and sex chromosome DNA are human specific, target specific and multiplex compatible. Having all three of these criteria represents a significant advantage over currently available methods. Our systems also include the first reported triplex PCR assay for the simultaneous quantification of nDNA, mtDNA and male Y DNA in a single PCR reaction. Mainstream application of these novel human specific multiplex PCR assays will undoubtedly be a valuable tool for forensic genomics.

What is claimed is:

1. A process for simultaneous quantitation of a human mitochondrial DNA and at least one of human nuclear DNA and human Y chromosome DNA in a sample, said process comprising the steps of:

performing multiplex polymerase chain reaction for simultaneously amplifying a region of the human mitochondrial DNA containing a human/chimp mismatch and a mitochondrial DNA/nuclear DNA mismatch by using a primer pair specific to human mitochondrial DNA, the region of the human mitochondrial DNA being not the hypervariable region, and at least one region of the human nuclear DNA containing a duplicated region of the Yb lineage of Alu subfamilies and an AluYb8 diagnostic base by using a primer pair specific to human nuclear DNA, and a region of the human Y chromosome DNA containing a 90 base pair sequence which is deleted on the human X-chromosome in an X-Y chromosome homologous region by using a primer pair specific to the human Y chromosome DNA in order to obtain an amplified products; and quantitating the human mitochondrial DNA, and at least one of the human nuclear DNA and the human Y chromosome DNA by comparing the amplified products with a reference standard.

2. The process of claim 1, wherein said at least one region includes both the human nuclear DNA and the human Y chromosome DNA.

3. The process of claim 1, wherein said at least one region is the human nuclear DNA.

4. The process of claim 2, wherein the primer pair amplifying the region of the human nuclear DNA comprises the following sequences:

```
5' CTTGCAGTGAGCCGAGATT 3';        (SEQ ID NO:13)
and

5' GAGACGGAGTCTCGCTCTGTC 3'.      (SEQ ID NO:14)
```

5. The process of claim 2, wherein the primer pair amplifying the region of the human Y chromosome DNA comprises the following sequences:

```
5' CACCTACTGTGCCAGACAATGTG 3';    (SEQ ID NO:16)
and

5' CCCATGCCATGTTTGTCATACT 3'.     (SEQ ID NO:17)
```

6. The process of claim 3, wherein the primer pair amplifying the region of the human mitochondrial DNA comprises the following sequences:

```
5' AATATTAAACACAAACTACCACCTACCT 3';  (SEQ ID NO:10)
and

5' TGGTTCTCAGGGTTTGTTATAA 3'.        (SEQ ID NO:11)
```

7. The process of claim 1, wherein the quantitation step comprises detecting the amplified products by using a quantitative PCR (qPCR) system.

8. The process of claim 1, wherein the quantitation step further compnses using a nucleotide probe for the quantitation of the human nuclear DNA, the nucleotide probe containing the following sequence:

```
5' ACTGCAGTCCGCAGTCCGGCCT 3'.     (SEQ ID NO:15)
```

9. The process of claim 1, wherein the quantitation step comprises using a nucleotide probe for the quantitation of the human nuclear DNA, the nucleotide probe containing the following sequence:

```
5'VIC ACTGCAGTCCGCAGTCCGGCCT3' MGBNFQ (5'VIC-SEQ ID NO:15-3'MGBNFQ).
```

10. The process of claim 2, wherein the quantitation step comprises using a nucleotide probe for the quantitation of the human Y chromosome DNA, the nucleotide probe containing the following sequence:

```
5' TAGGCTCTAGGAATACAAAA 3'.       (SEQ ID NO:18)
```

11. The process of claim 2, wherein the quantitation step comprises using a nucleotide probe for the quantitation of the human Y chromosome DNA, the nucleotide probe containing the following sequence:

```
5' NED TAGGCTCTAGGAATACAAAA 3' MGBNFQ (5' NED-SEQ
ID NO:18-3' MGBNFQ).
```

12. The process of claim 3, wherein the quantitation step comprises using a nucleotide probe for the quantitation of the human mitochondrial DNA, the nucleotide probe containing the following sequence:

```
5' CCTCACCAAAGCCCATA 3'.    (SEQ ID NO:12)
```

13. The process of claim 3, wherein the quantitation step comprises using a nucleotide probe for the quantitation of the human mitochondrial DNA, the nucleotide probe containing the following sequence:

```
5' FAM CCTCACCAAAGCCCATA 3'MGBNFQ
(5'FAM-SEQ ID NO:12-3'MGBNFQ).
```

14. A process for simultaneous quantitation of human nuclear DNA, human mitochondrial DNA and human Y chromosome DNA in a sample, said process comprising the steps of:
performing multiplex polymerase chain reaction to simultaneously amplify a region of the human nuclear DNA containing a human nuclear specific sequence by using a first primer pair specific to the human nuclear specific sequence, a region of the human mitochondrial DNA containing a human mitochondria specific sequence by using a second primer pair specific to the human mitochondria specific sequence, and a region of the human Y chromosome DNA containing a human Y chromosome specific sequence by using a third primer pair specific to the human Y chromosome specific sequence, the amplified region of the human nuclear DNA containing a duplicated region of the Yb lineage of Alu subfamilies and an AluYb8 diagnostic base at the 3' end of a forward primer of the first primer pair, the amplified region of the human mitochondrial DNA containing a human/chimp mismatch and a mitochondrial DNA/nuclear DNA mismatch, the region of the human mitochondrial DNA being not the hypervariable region, the amplified region of the human Y chromosome DNA containing a 90-bp sequence which is deleted on the X chromosome in an X-Y homologous region;
measuring the amplified products from the human nuclear DNA, the human mitochondrial DNA and the human Y chromosome DNA by using a first probe for the human nuclear DNA, a second probe for the human mitochondrial DNA, and a third probe for the human Y chromosome DNA, respectively; and
quantitating the human nuclear DNA, the human mitochondrial DNA and the human Y chromosome DNA by comparing the amplified products with a reference standard.

15. The process of claim 14, wherein the first primer pair amplifying the human nuclear DNA comprises the following sequences:

```
5' CTTGCAGTGAGCCGAGATT 3';   (SEQ ID NO:13)
and

5' GAGACGGAGTCTCGCTCTGTC 3'.  (SEQ ID NO:14)
```

16. The process of claim 14, wherein the first probe for the human nuclear DNA comprises the following sequence:

```
5' ACTGCAGTCCGCAGTCCGGCCT 3'.  (SEQ ID NO:15)
```

17. The process of claim 14, wherein the first probe for the human nuclear DNA comprises the following sequence:

```
5'VIC ACTGCAGTCCGCAGTCCGGCCT3' MGBNFQ
(5'VIC-SEQ ID NO:15-3'MGBNFQ).
```

18. The process of claim 14, wherein the second primer pair amplifying the human mitochondrial DNA comprises the following sequences:

```
5' AATATTAAACACAAACTACCACCTACCT 3';   (SEQ ID NO:10)
and

5' TGGTTCTCAGGGTTTGTTATAA 3'.    (SEQ ID NO:11)
```

19. The process of claim 14, wherein the second probe for the human mitochondrial DNA comprises the following sequence:

```
5' CCTCACCAAAGCCCATA 3'.    (SEQ ID NO:12)
```

20. The process of claim 14, wherein the second probe for the human mitochondrial DNA comprises the following sequence:

```
5' FAM CCTCACCAAAGCCCATA 3'MGBNFQ
(5' FAM-SEQ ID NO:12-3'MGBNFQ.
```

21. The process of claim 14, wherein the third primer pair amplifying the human Y chromosome DNA comprises the following sequences:

```
5' CACCTACTGTGCCAGACAATGTG 3';   (SEQ ID NO:16)
and

5' CCCATGCCATGTTTGTCATACT 3'.    (SEQ ID NO:17)
```

22. The process of claim 14, wherein the third probe for the human Y chromosome DNA comprises the following sequence:

```
5' TAGGCTCTAGGAATACAAAA 3'.   (SEQ ID NO:18)
```

23. The process of claim 14, wherein the third probe for the human Y chromosome DNA comprises the following sequence:

```
5' NED TAGGCTCTAGGAATACAAAA 3' MGBNFQ (5' NED-SEQ
ID NO:18 3' MGBNFQ).
```

24. A process for simultaneously quantitating human X and Y chromosome DNA in a sample, said process comprising the steps of:
performing duplex polymerase chain reaction to amplify a region in SEQ ID NO: 9 of human Y chromosome DNA containing a 90 base pair sequence which starts from position 85 on SEQ ID NO.9 and which is deleted on SEQ ID NO: 8 of the human X-chromosome in an X-Y chromosome homologous region by using a third primer pair specific to the human Y chromosome DNA and to amplify a region in SEQ ID NO: 8 of the human X chromosome DNA in the X-Y chromosome homologous region by using a fourth primer pair; and quantitating the human Y chromosome DNA and the human X chromosome DNA by comparing the amplified products with a reference standard.

25. The process of claim 24, wherein the third primer pair amplifying the human Y chromosome comprises the following sequences:

```
5' CACCTACTGTGCCAGACAATGTG 3';   (SEQ ID NO:16)
and

5' CCCATGCCATGTTTGTCATACT 3'.    (SEQ ID NO:17)
```

26. The process of claim 24, wherein the quantitation step comprises using a nucleotide probe for the quantitation of the human Y chromosome DNA, the nucleotide probe containing the following sequence:

```
5' TAGGCTCTAGGAATACAAAA 3'.      (SEQ ID NO:18)
```

27. The process of claim 24, wherein the quantitation step comprises using a nucleotide probe for the quantitation of the human Y chromosome DNA, the nucleotide probe containing the following sequence:

```
5' NED TAGGCTCTAGGAATACAAAA 3' MGBNFQ
(5' NED-SEQ ID NO:18-3'MGBNFQ).
```

28. The process of claim 24, wherein the fourth primer pair amplifying the human X chromosome comprises the following sequences:

```
5' CCACGAACTTTAATTAGTCACCTACTGT 3';  (SEQ ID NO:19)
and

5' ATTCCTCTCTCCATTATGTTCAATTACA 3'.  (SEQ ID NO:20)
```

29. The process of claim 24, wherein the quantitation step comprises using a nucleotide probe for the quantitation of the human X chromosome DNA, the nucleotide probe containing the following sequence:

```
5' CAGACAATGTGATAAATG 3'.        (SEQ ID NO:21)
```

30. The process of claim 24, wherein the quantitation step comprises using a nucleotide probe for the quantitation of the human X chromosome DNA, the nucleotide probe containing the following sequence:

```
5' VIC CAGACAATGTGATAAATG 3' MGBNFQ (5' VIC-SEQ ID
NO:21-3' MGBNFQ).
```

31. The process of claim 1, wherein said at least one region is the human Y chromosome DNA.

32. The process of claim 31, wherein the primer pair amplifying the region of the human Y chromosome DNA comprises the following sequences:

```
5' CACCTACTGTGCCAGACAATGTG 3';   (SEQ ID NO:16)
and

5' CCCATGCCATGTTTGTCATACT 3'.    (SEQ ID NO:17)
```

33. The process of claim 32, wherein the primer pair amplifying the region of the human mitochondrial DNA comprises the following sequences:

```
5' AATATTAAACACAAACTACCACCTACCT 3'; (SEQ ID NO:10)
and

5' TGGTTCTCAGGGTTTGTTATAA 3'.    (SEQ ID NO:11)
```

34. The process of claim 31, wherein the primer pair amplifying the region of the human mitochondrial DNA comprises the following sequences:
5'AATATTAAACACAAACTACCACCTACCT 3'(SEQ ID NO: 10); and
5'TGGTTCTCAGGGTTTGTTATAA 3'(SEQ ID NO: 11).

35. The process of claim 3, wherein the primer pair amplifying the region of the human nuclear DNA comprises the following sequences:

```
5' CTTGCAGTGAGCCGAGATT 3';       (SEQ ID NO:13)
and

5' GAGACGGAGTCTCGCTCTGTC 3'.     (SEQ ID NO:14)
```

36. The process of claim 35, wherein the primer pair amplifying the region of the human mitochondrial DNA comprises the following sequences:

```
5' AATATTAAACACAAACTACCACCTACCT 3'; (SEQ ID NO:10)
and

5' TGGTTCTCAGGGTTTGTTATAA 3'.    (SEQ ID NO:11)
```

37. The process of claim 2, wherein the primer pair amplifying the region of the human mitochondrial DNA comprises the following sequences:
5'AATATTAAACACAAACTACCACCTACCT 3'(SEQ ID NO: 10); and
5'TGGTTCTCAGGGTTTGTTATAA 3'(SEQ ID NO: 11);
the primer pair amplifying the region of the human nuclear DNA comprises the following sequences:

```
5' CTTGCAGTGAGCCGAGATT 3';       (SEQ ID NO:13)
and

5' GAGACGGAGTCTCGCTCTGTC 3'.     (SEQ ID NO:14)
``` the primer pair amplifying the region of the human Y chromosome DNA comprises the following sequences:

```
5' CACCTACTGTGCCAGACAATGTG 3';   (SEQ ID NO:16)
and

5' CCCATGCCATGTTTGTCATACT 3'.    (SEQ ID NO:17)
```

* * * * *

UNITED STATES PATENT AND TRADEMARK OFFICE
CERTIFICATE OF CORRECTION

PATENT NO. : 7,405,044 B2  Page 1 of 1
APPLICATION NO. : 11/245444
DATED : July 29, 2008
INVENTOR(S) : Jerilyn A. Walker et al.

It is certified that error appears in the above-identified patent and that said Letters Patent is hereby corrected as shown below:

Title Pg, Item
(74) Attorney, Agent, or Firm

Please correct "Robert E. Bushnessl, Esq."
      to -- Robert E. Bushnell, Esq. --

Signed and Sealed this

Sixteenth Day of September, 2008

JON W. DUDAS
*Director of the United States Patent and Trademark Office*

SEQUENCE LISTING

```
<160> NUMBER OF SEQ ID NOS: 21

<210> SEQ ID NO 1
<211> LENGTH: 87
<212> TYPE: DNA
<213> ORGANISM: Homo sapiens

<400> SEQUENCE: 1
gaacccggga ggcggagctt gcagtgagcc gagatcgcgc cactgcactc cagcctgggc      60
gacagagcga gactccgtct caaaaaa                                          87

<210> SEQ ID NO 2
<211> LENGTH: 94
<212> TYPE: DNA
<213> ORGANISM: Homo sapiens

<400> SEQUENCE: 2
gaacccggga agcggagctt gcagtgagcc gagattgcgc cactgcagtc cgcagtccgg      60
cctgggcgac agagcgagac tccgtctcaa aaaa                                  94

<210> SEQ ID NO 3
<211> LENGTH: 299
<212> TYPE: DNA
<213> ORGANISM: Homo sapiens

<400> SEQUENCE: 3
gcccgtattt accctatagc accccctcta cccctctag agcccactgt aaagctaact       60
tagcattaac cttttaagtt aaagattaag agaaccaaca cctctttaca gtgaaatgcc     120
ccaactaaat actaccgtat ggcccaccat aattacccc atactcctta cactattcct     180
catcacccaa ctaaaaatat taaacacaaa ctaccaccta cctccctcac caaagcccat     240
aaaaataaaa aattataaca aaccctgaga accaaaatga acgaaaatct gttcgcttc     299

<210> SEQ ID NO 4
<211> LENGTH: 299
<212> TYPE: DNA
<213> ORGANISM: Homo sapiens

<400> SEQUENCE: 4
gcccgtattt accctatagc accccctcta cccctctag agcccactgt aaagctaact       60
tagcattaac cttttaagtt aaagattaag agaaccaaca cctctttaca gtgaaatgcc     120
```

```
ccaactaaat actaccgtat gacccaccat aattacccccc atactcctta cactattcct    180
catcacccaa ctaaaaatat aaatacaaa ttaccaccta cctccctcac caaagcccat     240
aaaaataaaa aactataaca aaccctgaga accaaaatga acgaaaatct gttcacttc     299
```

<210> SEQ ID NO 5
<211> LENGTH: 300
<212> TYPE: DNA
<213> ORGANISM: Pan paniscus

<400> SEQUENCE: 5

```
acccgtattc actctataac accttctcta cccctctcca aagctcactg taaagctaac     60
ctagcattaa ccttttaagt taaagattaa gaggaccaac acctctttac agtgaaatgc    120
cccaactaaa taccgccgta tgacccacca caattacccc tatactcctt acactatttc    180
ttatcaccca actaaaaata ttaaactcaa attaccatct acccccctca ccaaaaccca    240
taaaaataaa aaactacaat aaaccctgag aaccaaaatg aacgaaaatc tgttcgcttc    300
```

<210> SEQ ID NO 6
<211> LENGTH: 300
<212> TYPE: DNA
<213> ORGANISM: Pan troglodytes

<400> SEQUENCE: 6

```
acccgtattc actctatagc accttctcta cccctctcca gagctcactg taaagctaac     60
ctagcattaa ccttttaagt taaagattaa gaggaccgac acctctttac agtgaaatgc    120
cccaactaaa taccgccgta tgacccacca taattacccc catactcctg acactatttc    180
tcgtcaccca actaaaaata ttaaattcaa attaccatct acccccctca ccaaaaccca    240
taaaaataaa aaactacaat aaaccctgag aaccaaaatg aacgaaaatc tattcgcttc    300
```

<210> SEQ ID NO 7
<211> LENGTH: 300
<212> TYPE: DNA
<213> ORGANISM: Gorilla gorilla

<400> SEQUENCE: 7

```
acccgtattc gccctataat accccctctca tccctctcca gagctcactg taaagctaac     60
ctagcgttaa ccttttaagt taaagattaa gagtatcggc acctctttgc agtgaaatgc    120
cccagctaaa taccaccgta tggcccacca taattgcccc aatactcctc acactatttc    180
tcattaccca actaaaagtt ttaaacacaa attaccacct acccccctta ccaaaaacta    240
taaaaataaa aaacttctgt aaaccctgag aaccaaaatg aacgaaaatt tattcgcttc    300
```

<210> SEQ ID NO 8
<211> LENGTH: 160
<212> TYPE: DNA
<213> ORGANISM: Homo sapiens

<400> SEQUENCE: 8

```
aatttaaagg aggtgtcatc cctgtatttg ttcactgaag agtccacgaa ctttaattag     60
tcacctactg tgccagacaa tgtgataaat ggtgtaattg aacataatgg agagaggaat    120 taattttttgt taagaggttg agaagaggtt cataaaggag                          160
```

<210> SEQ ID NO 9
<211> LENGTH: 250
<212> TYPE: DNA
<213> ORGANISM: Homo sapiens

<400> SEQUENCE: 9

```
aatttaaagg aggtgtcatc cctgtatttg ttcactgagg agtccacaaa ctttaattag    60
tcacctactg tgccagacaa tgtgctaggc tctaggaata caaaagagag tatgacaaac   120
atggcatggg cctctttgag ccatgacact cttatagatc taggatacga tgtgataaat   180
gatgtaattg aacataatgg agagaggaat taattttgt taagaggttg agaagaggtt    240
cataaaggag                                                          250
```

<210> SEQ ID NO 10
<211> LENGTH: 28
<212> TYPE: DNA
<213> ORGANISM: Artificial
<220> FEATURE:
<223> OTHER INFORMATION: Forward primer for human mitochondrial DNA
      quantitation assay, incorporating human/chimp mismatch at the 3'
      end

<400> SEQUENCE: 10

```
aatattaaac acaaactacc acctacct                                       28
```

<210> SEQ ID NO 11
<211> LENGTH: 22
<212> TYPE: DNA
<213> ORGANISM: artificial
<220> FEATURE:
<223> OTHER INFORMATION: Reverse primer for human mitochondrial DNA
      quantitation assay, incorporating human/chimp mismatch at the 3'
      end and a single mtDNA/nuclear DMA mismatch at the 3'end

<400> SEQUENCE: 11

```
tggttctcag ggtttgttat aa                                             22
```

<210> SEQ ID NO 12
<211> LENGTH: 17
<212> TYPE: DNA
<213> ORGANISM: artificial
<220> FEATURE:
<223> OTHER INFORMATION: Probe for human mitochondrial DNA quantitation
      assay

<400> SEQUENCE: 12

```
cctcaccaaa gcccata                                                   17
```

<210> SEQ ID NO 13
<211> LENGTH: 19
<212> TYPE: DNA
<213> ORGANISM: artificial
<220> FEATURE:
<223> OTHER INFORMATION: Forward primer for human nuclear DNA
      quantitation assay, incorporating the 7-bp duplicated region
      characteristic of the Yb lineage of Alu subfamilies and an AluYb8
      diagnostic base at the 3'end

<400> SEQUENCE: 13

```
cttgcagtga gccgagatt                                                 19
```

<210> SEQ ID NO 14
<211> LENGTH: 21
<212> TYPE: DNA
<213> ORGANISM: artificial
<220> FEATURE:
<223> OTHER INFORMATION: Reverse primer for human nuclear DNA
      quantitation assay

<400> SEQUENCE: 14

```
gagacggagt ctcgctctgt c                                              21

<210> SEQ ID NO 15
<211> LENGTH: 22
<212> TYPE: DNA
<213> ORGANISM: artificial
<220> FEATURE:
<223> OTHER INFORMATION: Probe for human nuclear DNA quantitation assay

<400> SEQUENCE: 15
actgcagtcc gcagtccggc ct                                             22

<210> SEQ ID NO 16
<211> LENGTH: 23
<212> TYPE: DNA
<213> ORGANISM: artificial
<220> FEATURE:
<223> OTHER INFORMATION: Forward primer for the sex chromosome assay,
      designed around a 90-bp deletion on the human X chromosome in an
      X-Y homologous region

<400> SEQUENCE: 16
cacctactgt gccagacaat gtg                                            23

<210> SEQ ID NO 17
<211> LENGTH: 22
<212> TYPE: DNA
<213> ORGANISM: artificial
<220> FEATURE:
<223> OTHER INFORMATION: Reverse primer for the sex chromosome assay,
      designed around a 90-bp deletion on the human X chromosome in an
      X-Y homologous region

<400> SEQUENCE: 17
cccatgccat gtttgtcata ct                                             22

<210> SEQ ID NO 18
<211> LENGTH: 20
<212> TYPE: DNA
<213> ORGANISM: artificial
<220> FEATURE:
<223> OTHER INFORMATION: Probe for the sex chromosome assay

<400> SEQUENCE: 18
taggctctag gaatacaaaa                                                20

<210> SEQ ID NO 19
<211> LENGTH: 28
<212> TYPE: DNA
<213> ORGANISM: artificial
<220> FEATURE:
<223> OTHER INFORMATION: Forward primer for the sex chromosome assay,
      designed around a 90-bp deletion on the human X chromosome in an
      X-Y homologous region

<400> SEQUENCE: 19
ccacgaactt taattagtca cctactgt                                       28

<210> SEQ ID NO 20
<211> LENGTH: 28
<212> TYPE: DNA
<213> ORGANISM: artificial
<220> FEATURE:
<223> OTHER INFORMATION: Reverse primer for the sex chromosome assay,
      designed around a 90-bp deletion on the human X chromosome in an
      X-Y homologous region
```

-continued

```
<400> SEQUENCE: 20
attcctctct ccattatgtt caattaca                                          28

<210> SEQ ID NO 21
<211> LENGTH: 18
<212> TYPE: DNA
<213> ORGANISM: artificial
<220> FEATURE:
<223> OTHER INFORMATION: Probe for the sex chromosome assay

<400> SEQUENCE: 21
cagacaatgt gataaatg                                                     18
```